(12) United States Patent
McClintock

(10) Patent No.: US 10,806,494 B2
(45) Date of Patent: Oct. 20, 2020

(54) FIXATION DEVICES, FIXATION SYSTEMS, AND METHODS OF USING THE SAME

(71) Applicant: K2M, Inc., Leesburg, VA (US)

(72) Inventor: Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 125 days.

(21) Appl. No.: 16/083,198

(22) PCT Filed: Mar. 8, 2017

(86) PCT No.: PCT/US2017/021349
§ 371 (c)(1),
(2) Date: Sep. 7, 2018

(87) PCT Pub. No.: WO2017/156121
PCT Pub. Date: Sep. 14, 2017

(65) Prior Publication Data
US 2019/0090909 A1      Mar. 28, 2019

Related U.S. Application Data

(60) Provisional application No. 62/305,028, filed on Mar. 8, 2016.

(51) Int. Cl.
*A61B 17/70* (2006.01)
*A61B 17/84* (2006.01)
*A61B 17/86* (2006.01)

(52) U.S. Cl.
CPC ........ *A61B 17/7035* (2013.01); *A61B 17/844* (2013.01); *A61B 17/8625* (2013.01); *A61B 17/861* (2013.01)

(58) Field of Classification Search
CPC .............. A61B 17/7035; A61B 17/844; A61B 17/8625; A61B 17/861; A61B 17/866;
(Continued)

(56) References Cited

U.S. PATENT DOCUMENTS

| 5,334,204 A | * | 8/1994 | Clewett | A61B 17/8625 606/312 |
| 6,162,691 A | * | 12/2000 | Huang | H01L 29/665 257/E21.438 |

(Continued)

FOREIGN PATENT DOCUMENTS

| DE | 102011055106 | * | 4/2013 | ........... A61F 2/3662 |
| DE | 102011055106 B3 | | 4/2013 | |

OTHER PUBLICATIONS

International Search Report and Written Opinion dated May 19, 2017 issued in corresponding PCT Appln. No. PCT/US2017/021349.

*Primary Examiner* — Pedro Philogene
(74) *Attorney, Agent, or Firm* — Lerner, David, Littenberg, Krumholz & Mentlik, LLP

(57) ABSTRACT

A fixation device includes an outer member, a retaining member, and an inner member. The outer member includes an elongated body portion defining a central bore through at least a portion thereof that extends along a central longitudinal axis. The elongated body portion includes a slot defined therethrough. The retaining member is disposed within the outer member when in an initial position and extends through the slot of the outer member when in a deployed position. The inner member includes a cam shaft body disposed within the central bore of the outer member. The cam shaft body is coupled to the retaining member such that rotation of the inner member moves the retaining member between the initial and deployed positions.

30 Claims, 5 Drawing Sheets

(58) Field of Classification Search
CPC ... A61B 17/864; A61B 17/7055; A61B 17/68; A61B 17/8685; A61B 17/00; A61B 17/7032; A61B 17/84; A61B 2017/681; A61B 2017/8655; A61B 2017/0432; A61B 2017/0403; A61B 2017/0401; A61B 2017/0409; A61F 2/00; A61F 2/3662; A61F 2/3676; A61F 2002/0852; A61F 2002/0858; A61F 2002/0882; A61F 2002/0835; A61F 2002/30471; A61F 2002/30579; A61F 2002/30795; A61F 2002/4619
USPC .......... 606/1, 53, 57, 63, 104, 300–328, 606/246–279; 623/13.12
See application file for complete search history.

(56) References Cited

U.S. PATENT DOCUMENTS

| | | | |
|---|---|---|---|
| 7,461,574 B2 | 12/2008 | Lewis et al. | |
| 7,846,162 B2* | 12/2010 | Nelson | A61B 17/7208 606/62 |
| 8,038,701 B2* | 10/2011 | Rock | A61B 17/7032 606/266 |
| 8,062,374 B2 | 11/2011 | Markworth et al. | |
| 9,125,696 B2* | 9/2015 | Linke | A61B 17/74 |
| 2011/0213423 A1* | 9/2011 | Biedermann | A61B 17/8625 606/304 |
| 2014/0200587 A1 | 7/2014 | Pompee et al. | |

* cited by examiner

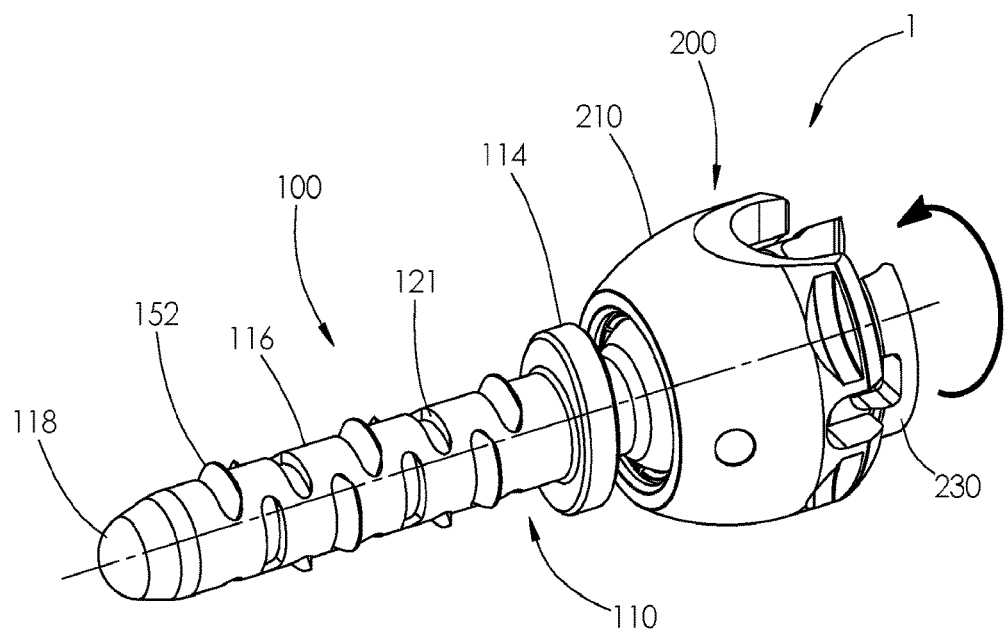
FIG. 7A
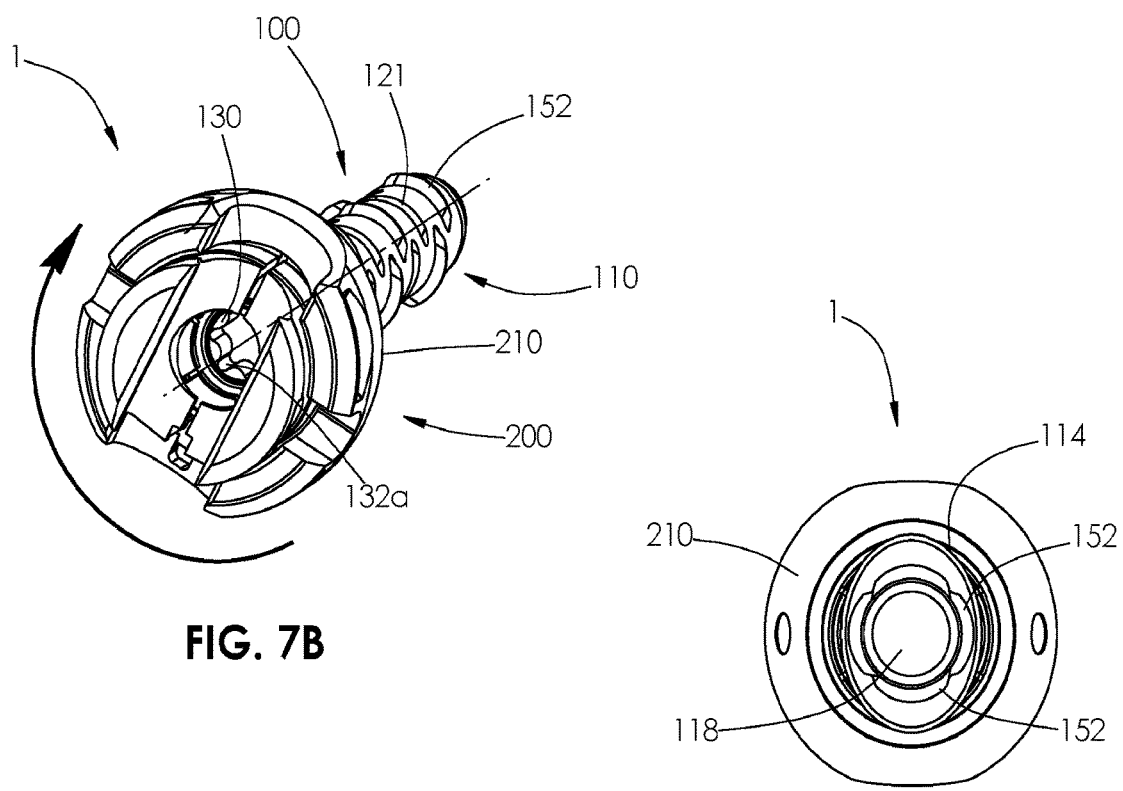
FIG. 7B
FIG. 7C

FIXATION DEVICES, FIXATION SYSTEMS, AND METHODS OF USING THE SAME

CROSS-REFERENCE TO RELATED APPLICATIONS

This application claims the benefit of, and priority to, U.S. Provisional Patent Application Ser. No. 62/305,028, which was filed on Mar. 8, 2016, the entire contents of which are hereby incorporated herein by reference.

TECHNICAL FIELD

The present disclosure relates generally to a fixation device, and more particularly, to fixation devices, fixation systems, and methods for securing fixation devices and systems to osseous tissue.

BACKGROUND

The human spine is the supporting axis of the body and makes all the movement of a person's head, arms, and legs possible. It is a highly flexible structure, capable of a high degree of curvature and twist in nearly every direction. An adult spine generally has twenty-four vertebrae, which can be categorized into three major sections. These categories include the cervical spine, the thoracic spine, and the lumbar spine. The cervical spine includes the upper seven vertebrae, the thoracic spine includes the next twelve vertebrae, and the lumbar spine includes the final five vertebrae. Below the lumbar spine is a bone called the sacrum, which is part of the pelvis. Muscles and ligaments are attached to a slender projection from the back of the vertebrae known as the spinous process. Housed within a narrow channel in the center of the spine is the spinal cord. All the nerves of the body are connected to the spinal cord.

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

Depending upon how such systems are coupled to the spine, the systems may be classified as anterior, posterior, or lateral implants. For example, lateral and anterior systems are coupled to the anterior portion of the spine. Posterior systems generally include a pair of rods that are fixed to adjacent vertebrae with pedicle screws on either side of the spinous process along a section of the spine. Depending upon the number and length of the pedicle screws used during a procedure, the insertion of the pedicle screws into the vertebrae can be a very time consuming and labor intensive part of the procedure. In particular, each pedicle screw requires several rotations by a user before it is fully inserted into a vertebra.

SUMMARY

In accordance with an aspect of the present disclosure, a fixation member includes an outer member, a retaining member, and an inner member. The outer member includes an elongated body portion defining a central bore through at least a portion thereof that extends along a central longitudinal axis. The elongated body portion includes a slot defined therethrough. The retaining member is disposed within the outer member when in an initial position and extends through the slot of the outer member when in a deployed position. The inner member includes a cam shaft body disposed within the central bore of the outer member. The cam shaft body is coupled to the retaining member such that rotation of the inner member moves the retaining member between the initial and deployed positions.

The outer member may include a head portion disposed proximal to the elongated body portion, and a proximal portion of the central bore may be disposed within the head portion. In embodiments, the outer member includes a flange disposed between the head portion and the elongated body portion, the flange having a transverse dimension that is greater than a transverse dimension of the elongated body portion.

In some embodiments, the inner member includes a head disposed proximal to the cam shaft body, and the head is positioned within the proximal portion of the central bore. The head of the inner member may be concentric with the proximal portion of the central bore. In certain embodiments, the head of the inner member includes a proximal end including a recessed drive feature. The inner member may include an elongated neck disposed between the head and the cam shaft body.

The outer member may include a distal tip disposed distal to the elongated body portion, and a distal portion of the central bore may be disposed within the distal tip. In embodiments, the inner member includes a tail disposed distal to the cam shaft body, and the tail is positioned within the distal portion of the central bore. In some embodiments, the tail is offset with respect to the central longitudinal axis and disposed within an eccentric opening of a bearing that is positioned in the distal portion of the central bore. In certain embodiments, the bearing is concentric with the distal portion of the central bore.

The cam shaft body of the inner member may include an eccentric segment that is offset with respect to the central longitudinal axis. The retaining member may define an eccentric bore therethrough that receives the eccentric segment of the cam shaft body such that rotation of the inner member causes the eccentric segment to rotate about the central longitudinal axis which, in turn, moves the retaining member laterally.

The retaining member may include an engagement surface configured to cut or thread into osseous tissue as the retaining member is moved from the initial position to the deployed position. In embodiments, the engagement surface includes a first side and a second side terminating at an edge. In some embodiments, at least one of the first or second sides is angled. In certain embodiments, the edge is a blade.

The fixation device may include a plurality of retaining members, and the elongated body of the outer member may include a plurality of slots. In embodiments, the plurality of slots is arranged in rows, and each row includes two slots of the plurality of slots disposed in opposed relation relative to each other. In some embodiments, the two slots of each row are disposed at about 90° relative to the two slots in an adjacent row.

In embodiments, the cam shaft body includes a plurality of eccentric segments each laterally offset with respect to the central longitudinal axis of the outer member. In some embodiments, each eccentric segment of the plurality of eccentric segments extends through an eccentric bore defined through a retaining member of the plurality of retaining members such that rotation of the inner member causes the eccentric segments to rotate about the central longitudinal axis which, in turn, laterally moves the retaining members between the initial and deployed positions.

In accordance with another aspect of the present disclosure, a fixation system may include the fixation device and a modular attachment device secured to the outer member of the fixation device.

In embodiments, the outer member includes a head portion disposed proximal to the elongated body portion, and the head portion supports the modular attachment device thereon. In some embodiments, the modular attachment device is pivotably mounted on the head portion of the outer member. The modular attachment device may be a housing assembly.

In accordance with yet another aspect of the present disclosure, a method of securing a fixation device to osseous tissue includes inserting an elongated body portion of an outer member of a fixation device into a hole in osseous tissue, the elongated body portion defining a central bore through at least a portion thereof that extends along a central longitudinal axis, the elongated body portion including a slot defined therethrough, and rotating an inner member of the fixation device that is disposed within the central bore of the outer member, the inner member including a cam shaft body coupled to a retaining member of the fixation device that is disposed within the outer member in an initial position, the rotation of the inner member moving the retaining member to a deployed position in which the retaining member extends through the slot of the outer member and cuts or threads into the osseous tissue surrounding the hole.

The method may include abutting a distal surface of a flange of the outer member, which is disposed proximal to the elongated body portion, against the osseous tissue to limit the insertion depth of the elongated body portion into the hole.

In embodiments, the method includes rotating the outer member of the fixation device after rotating the inner member such that the deployed retaining member further cuts or threads through the osseous tissue.

In some embodiments, the method includes attaching a modular attachment device to a head portion of the outer member, the head portion disposed proximal to the elongated body portion.

Other aspects, features, and advantages will be apparent from the description, drawings, and the claims.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein:

FIG. 7A is a perspective, side view of the fixation system of FIG. 5, shown in a deployed position;

FIG. 7B is a perspective, end view of the fixation system of FIG. 7A; and

FIG. 7C is an end view of the fixation system of FIGS. 7A and 7B.

DETAILED DESCRIPTION

Figure 1:
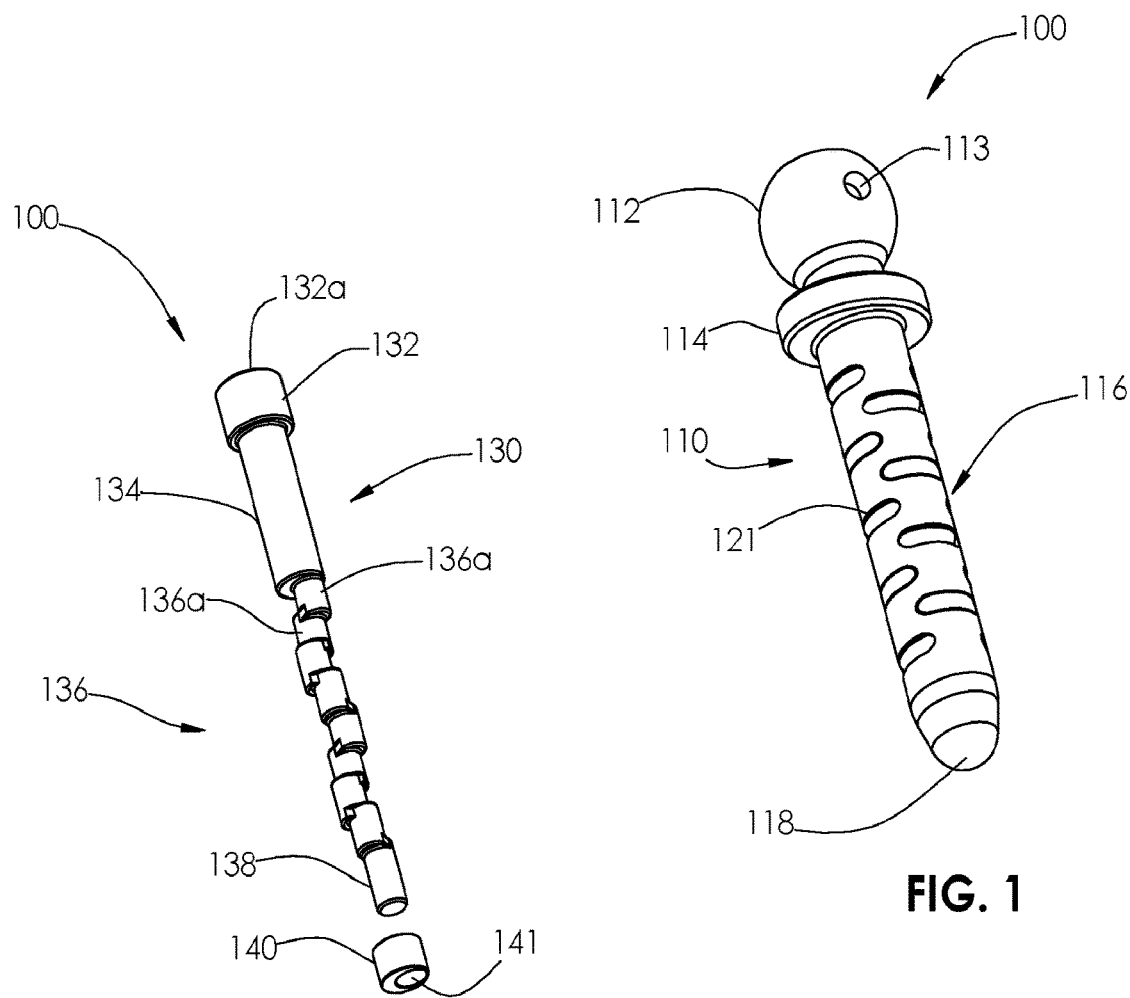
FIG. 1 is a perspective view of a fixation device in accordance with an embodiment of the present disclosure, shown in an initial position.

Exemplary embodiments of the present disclosure are discussed herein below in terms of a fixation device for use in osseous tissue. The fixation device is fully inserted into osseous tissue with minimal and/or reduced time and/or effort compared to fixation devices including threaded outer surfaces (e.g., traditional bone screws) by, for example, limiting the rotational effort required for insertion of the fixation device into tissue.

While the principles of the present disclosure are described below with respect to the insertion of a fixation device into a pedicle of a vertebra during orthopedic spine surgery, it should be understood that the fixation device of the present disclosure is suitable for insertion into any osseous tissue, such as the iliac of the pelvis, and use in a variety of surgical procedures. Accordingly, a person of ordinary skill in the art will readily appreciate that the size and/or shape of the fixation device, or components thereof, can be modified for proper alignment and fit within a desired osseous tissue. For example, the fixation device may be shorter in length than a traditional bone screw. As another example, if the osseous tissue is a pedicle of a vertebra, the fixation device can be sized and dimensioned so that it would not extend into the intervertebral space.

The embodiments of the present disclosure are now described in detail with reference to the drawings in which like reference numerals designate identical or corresponding elements in each of the several views. Throughout this description, the term "proximal" refers to a portion of a system, device, or component thereof that is closer to a clinician, and the term "distal" refers to the portion of the system, device, or component thereof that is farther from the clinician. The term "clinician" refers to a doctor (e.g., a surgeon), a nurse, or any other care provider, and may include support personnel.

Figure 2:
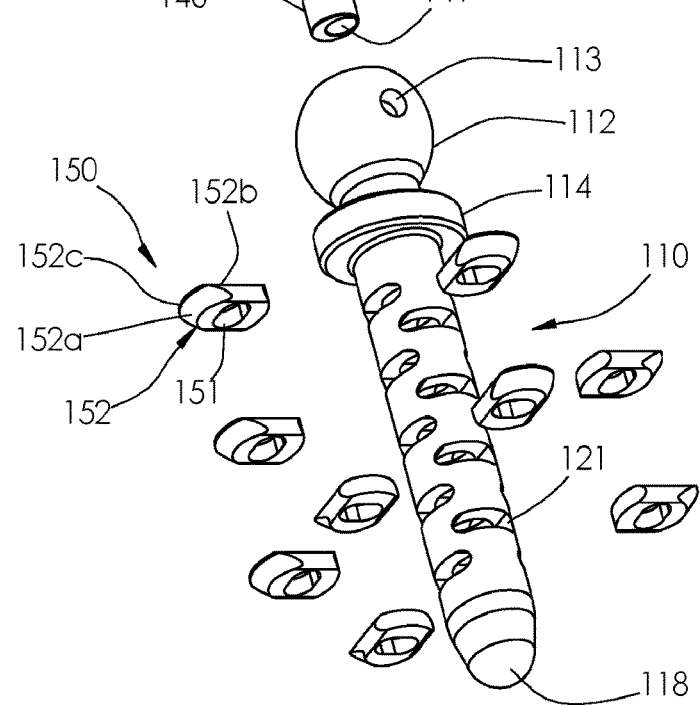
FIG. 2 is an exploded view, with parts separated, of the fixation device of FIG. 1.

Referring now to FIGS. 1 and 2, a fixation device 100 in accordance with an embodiment of the present disclosure is shown. The fixation device 100 includes an outer member 110, an inner member 130, and at least one retaining member 150. The fixation device 100 is suitable for use during the treatment of bones (e.g., to fix the position of a bone, or portions thereof, or to maintain alignment of bone(s)), and may provide a point of fixation and/or facilitate the attachment of other devices (e.g., rods, plates, etc.) to the bone(s).

The fixation device 100 is formed from biocompatible material(s) including, but not limited to, metals, such as titanium, titanium alloy, stainless steel, nickel titanium, and cobalt chrome, as well as polymers, such as polyetheretherketone, or combinations thereof.

Figure 3A:
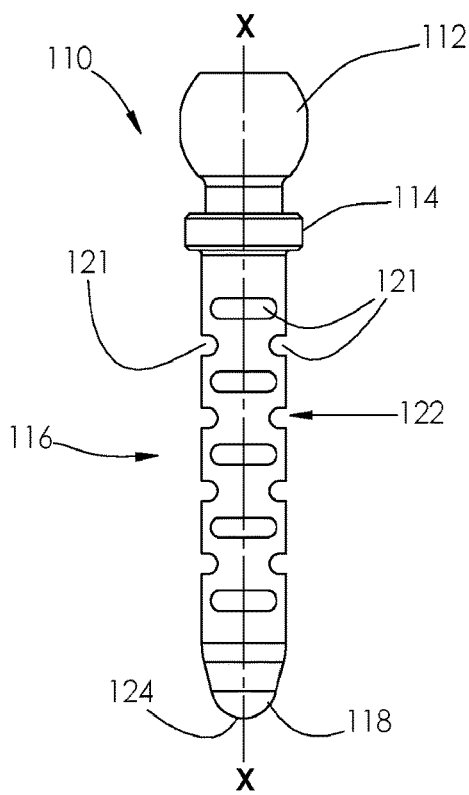
FIGS. 3A and 3B are side views of an outer member of the fixation device of FIG. 1.
Figure 3B:
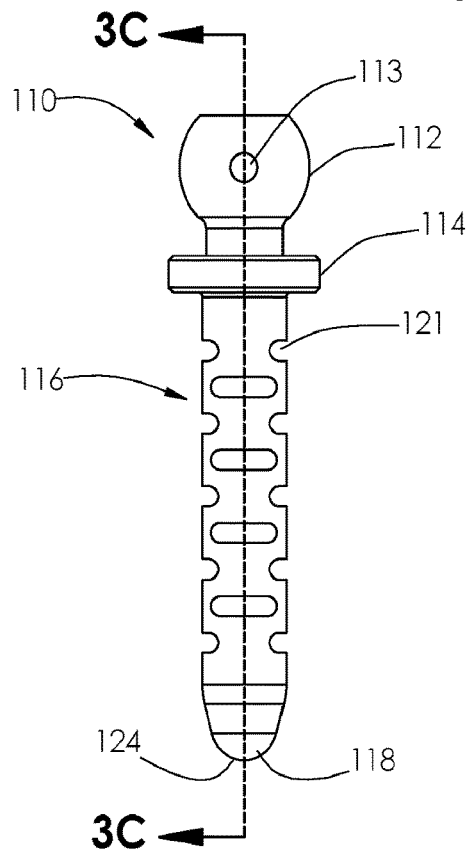
Figure 3C:
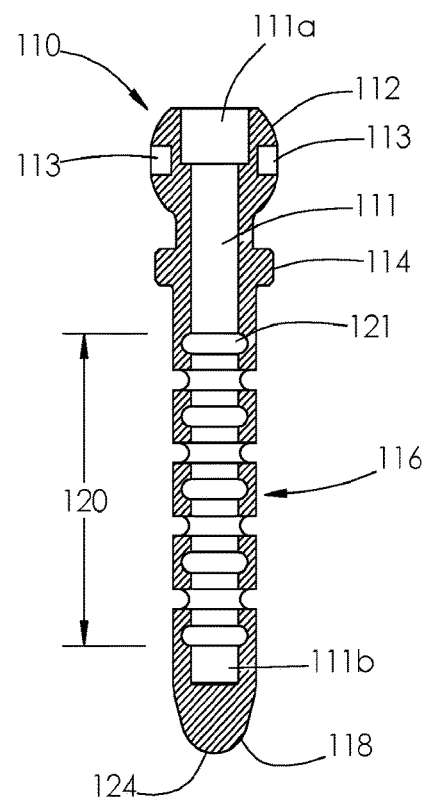
FIG. 3C is a cross-sectional view of the outer member of FIGS. 3A and 3B, taken along line 3C-3C of FIG. 3B.

As shown in FIGS. 3A-3C, the outer member 110 extends along a central longitudinal axis "X" and includes a head portion 112, a flange 114, an elongated body portion 116, and a distal tip 118. The outer member 110 may be integrally formed (e.g., by machining, molding, etc.), or one or more of the head portion 112, the flange 114, the elongated body portion 116, and/or the distal tip 118 may be fixedly attached (e.g., by welding, fastening, press-fitting, etc.) to an adjacent component of the outer member 110 such that the outer member 110 has a one-piece construction. For example, the distal tip 118 may be press fit or welded onto the elongated body portion 116 of the outer member 110.

A central bore 111 extends at least partially through the outer member 110 and is concentric with the central longitudinal axis "X". As specifically shown in FIG. 3C, the central bore 111 extends through the head portion 112, the flange 114, the elongated body portion 116, and terminates within the distal tip 118. It should be understood, however, that the central bore 111 may extend through the entire length of the outer member 110 such that the distal tip 118 is open, or may terminate at any point within the elongated body portion 116 distal to a slotted region 120 of the elongated body portion 116.

As also shown in FIG. 3C, a proximal portion 111a of the central bore 111, which is disposed within the head portion 112 of the outer member 110, has a larger diameter than the remaining portion of the central bore 111. The proximal portion 111a of the central bore 111 is dimensioned to accommodate a head 132 (FIG. 2) of the inner member 130. It should be understood that the central bore 111 may have a constant diameter or a varying diameter (e.g., stepped regions, tapering regions, etc.) along the length thereof, so long as the central bore 111 is configured to accommodate the inner member 130 and the retaining members 150 therein, as described in further detail below.

With continued reference to FIGS. 3A-3C, the head portion 112 of the outer member 110 has a substantially spherical or ball shape and includes recesses 113 defined in an outer surface thereof that are opposed and aligned with each other. The head portion 112 is configured to facilitate attachment between the fixation device 100 and another surgical device, such as a modular attachment device 200 (see e.g., FIG. 5), as described in further detail below. The spherical shape of the head portion 112 can facilitate multi or polyaxial movement of the fixation device 100 relative to the other surgical device when coupled thereto, and the recesses 113 are configured to receive a connecting member (e.g., a pin) therein for the attachment of the other surgical devices to the fixation device 100. The head portion 112, however, may be any shape and/or size (e.g., a threaded shaft) that can act as a connection area for the attachment of other surgical devices thereto, and may include one or more recesses 113 for connecting the other surgical device to the head portion 112, as also described in further detail below.

The flange 114 of the outer member 110 is disposed between the head portion 112 and the elongated body portion 116. The flange 114 separates the head portion 112 which, as described above, may act as a connection portion of the fixation device 100 to other surgical devices, and the elongated body portion 116 which acts as an anchoring portion of the fixation device 100 in tissue. The flange 114 has an outer dimension that is greater than the outer dimension of the elongated body 116 such that the flange 114 may be used as a guide to ensure that the fixation device 100 is properly positioned within, and fully inserted into, an osseous tissue. For example, the flange 114 may limit the depth of insertion of the fixation device 100 into osseous tissue when a distal surface of the flange 114 abuts against an exterior surface of osseous tissue. While the flange 114 is shown as having an elliptical shape, the flange 114 may have any suitable size and/or shape (e.g., circular or non-circular), and may be larger than a targeted opening in osseous tissue. Further, if the fixation device 100 is to be inserted into a pedicle, the flange 114 may be sized and shaped to be larger than an end of the pedicle.

The elongated body portion 116 of the outer member 110 is substantially tubular in shape. The elongated body portion 116, however, may have any shape, size, and/or length suitable for insertion into the targeted opening in osseous tissue. The elongated body portion 116 includes a slotted region 120 extending along at least a portion of the length thereof. The slotted region 120 may extend the entire length of the elongated body portion 116, a portion of the length of the elongated body portion 116, or include a plurality of slotted regions 120 disposed in spaced relation relative to each other along the length of the elongated body portion 116.

The slotted region 120 includes one or more slots 121 defined through an outer surface of the elongated body portion 116. The slots 121 are arranged in rows 122, with each row 122 having a pair of the slots 121 disposed in opposed and aligned relation relative to each other. The slots 121 in each row 122 are disposed at about 90° with respect to slots 121 in an adjacent row 122 such that each slot 121 is offset about 90° from the slots 121 defined in the adjacent rows 122. The slotted region 120 may include any number of slots 121 configured in any desired arrangement about the elongated body portion 116.

The slots 121 are defined through the elongated body portion 116 along an axis that is substantially parallel to the flange 114 (e.g., transverse to the central longitudinal axis "X") and have an elongated (e.g., oblong or elliptical) shape. The slots 121 are configured to allow for the passage of engagement surfaces 152 (FIG. 2) of the retaining members 150 therethrough. It should be understood that the configuration, number, and/or orientation of the slots 121 may vary, depending upon the configuration and number of retaining members 150 utilized in the fixation device 100. For example, the slots 121 may be dimensioned to have a complementary geometry with the engagement surfaces 152 of the retaining members 150.

The distal tip 118 of the outer member 110 tapers towards a semispherical, closed blunt end 124 such that the distal tip 118 is atraumatic and guides the elongated body portion 116 through osseous tissue, as well as preventing the inner member 130 (FIG. 2) from extending beyond the blunt end 124 of the outer member 110. The distal tip 118, however, may have other configurations. For example, as discussed above, the central bore 111 of the outer member 110 may extend through the distal tip 118 such that the distal tip 118 is open. As another example, the distal tip 118 may be conical in shape and/or may have a pointed end.

Referring again to FIG. 2, the inner member 130 includes, as viewed from proximal to distal, a cap or head 132, an elongated neck 134, a cam shaft body 136, and a tail 138. The inner member 130 may be integrally formed (e.g., by machining, molding, etc.), or one or more of the head 132, the elongated neck 134, the cam shaft body 136, and/or the tail 138 may be fixedly attached (e.g., by welding, fastening, press-fitting, etc.) to an adjacent component of the inner member 130 such that the inner member 130 has a one-piece construction. For example, the head 132 may be press fit or welded onto the elongated neck 134 of the inner member 130. As another example, eccentric segments or cam lobes 136a of the cam shaft body 136 may fastened to an adjacent eccentric segment 136a of the cam shaft body 136.

The inner member 130 is configured and dimensioned to fit within the central bore 111 (FIG. 3C) of the outer member 110. As described in further detail below, when the fixation device 100 is assembled, the head 132 and the elongated neck 134 of the inner member 130 are concentric with the central longitudinal axis "X" of the outer member 110, and the cam shaft body 136 and the tail 138 are offset with respect to the central longitudinal axis "X".

The head 132 of the inner member 130 has a larger diameter than the elongated neck 134, the cam shaft body 136, and the tail 138, and is dimensioned to fit within the head portion 112 of the inner member 110. Specifically, the head 132 has an outer dimension that is complementary to the inner dimension of the proximal portion 111a of the central bore 111 of the outer member 110 to aid in retaining the head 132 within the head member 112, as well as supporting and maintaining alignment of the inner member 130 within the outer member 110 during rotation of the inner member 130. It should be understood, however, that the head 132 may have any size and/or shape that is capable of being retained within the head portion 112 of the outer member 110.

A proximal end 132a of the head 132 includes a female drive feature (FIG. 4B) that is configured to engage a complementary male drive feature (not shown) of a driving instrument as is known in the art. The female drive feature may be a recessed hex feature, e.g., hexagonal or hexolobular in shape, or any other suitable configuration that is engageable with a suitable driving instrument to enable the driving instrument to control rotation of the inner member 130 and/or aid in the deployment or retraction of the retaining members 150 from within the outer member 110.

With continued reference to FIG. 2, the elongated neck 134 of the inner member 130 is sized and shape to fit within a portion of the central bore 111 of the outer member 110 that extends from the head portion 112, through the flange 114, and into a portion of the elongated body portion 116 proximal to the slotted region 120. Similar to the head 132, the elongated neck 134 has an outer dimension that is complementary to the inner dimension of the corresponding portion of the central bore 111 of the outer member 110 to aid in supporting and maintaining alignment of the inner member 130 within the outer member 110 during rotation of the inner member 130. Accordingly, the elongated neck 134 may have any size and/or shape complementary to the geometry of the central bore 111 of the outer member 110.

The cam shaft body 136 of the inner member 130 includes a plurality of eccentric segments 136a that are each offset with respect to the central longitudinal axis "X" of the outer member 110. Each of the eccentric segments 136a is configured to extend through an eccentric opening 151 defined through a retaining member 150. It should be understood that the position of each of the eccentric segments 136a with respect to the central longitudinal axis "X" may vary depending on the configuration of the retaining members 150.

The tail 138 of the inner member 130 is dimensioned to fit within an eccentric opening 141 defined through a bearing 140 which is sized and shaped to fit a distal portion 111b (FIG. 3C) of the central bore 111 of the outer member 110. When the inner member 130 is rotated within the central bore 111 of the outer member 110, the bearing 140 enables the tail 138 to rotate in an eccentric manner (e.g., radially around the central longitudinal axis "X"). The bearing 140 has an outer dimension that is complementary to the inner dimension of the distal portion 111b of the central bore 111 of the outer member 110 to aid in supporting and maintaining alignment of the inner member 130 within the outer member 110 during rotation of the inner member 130. Accordingly, the inner member 130 is supported in both the proximal and distal portions 111a, 111b of the central bore 111 of the outer member 110.

Figure 4A:
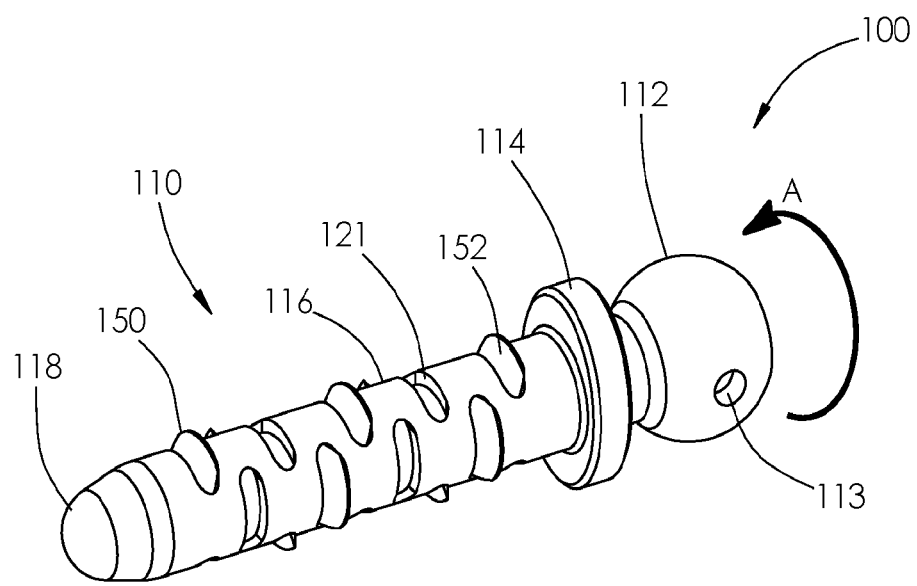
FIGS. 4A and 4B are perspective views of the fixation device of FIG. 1, shown in a deployed position.
Figure 4B:
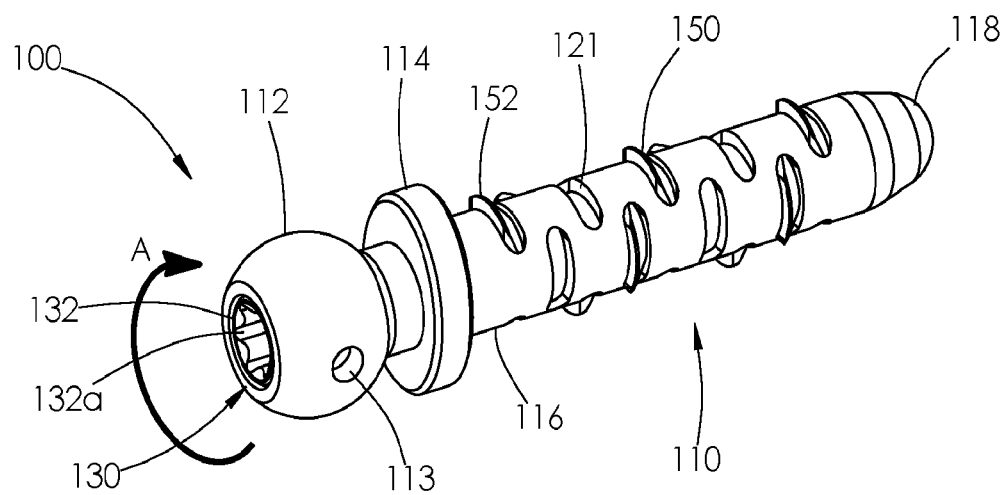

With continued reference to FIG. 2, the fixation device 100 includes at least one retaining member 150 configured and dimensioned to be retained within the central bore 111 of the outer member 110 when the fixation device 100 is in an initial or retracted position (FIG. 1), and to extend laterally through a slot 121 of the outer member 110 when the fixation device 100 is in a deployed or extended position (FIGS. 4A and 4B). In embodiments, the fixation device 100 includes a retaining member 150 associated with each slot 121 of the outer member 110. The number and/or arrangement of the retaining members 150 and/or slots 121 can vary, for example, to change insertion depth, amount of tissue purchase, and/or to accommodate anatomical differences of a patient.

Each retaining member 150 includes an eccentric bore 151 defined axially therethrough, and an engagement surface 152 including opposed first and second sides 152a, 152b terminating at an edge 152c. One or both of the first and second sides 152a, 152b may be angled such that the edge 152c defines a blade which can cut and/or thread into osseous tissue.

The retaining members 150 are positioned within a respective slot 121 of the outer member 110 and are sized and shaped to be fully disposed within the outer member 110 when in an initial position (FIG. 1) such that the edges 152c of the retaining members 150 do not extend beyond the outer member 110 (e.g., flush with the outer surface of the outer member 110). The retaining members 150 are configured to move laterally such that the engagement surfaces 152 of the retaining members 150 are deployed through the slots 121 of the outer member 110 when in a deployed position (FIGS. 4A and 4B). Specifically, the eccentric segments 136a of the cam shaft body 136 extend through respective eccentric bores 151 of the retaining members 150 such that rotation of the inner member 130 causes the eccentric segments 136a of the cam shaft body 136 to rotate around the central longitudinal axis "X" of the outer member 110 which, in turn, laterally displaces the retaining members 150 and pushes the engagement surfaces 152 through the slots 121 of the outer member 110.

With reference again to FIG. 1, the fixation device 100 is shown in an initial or undeployed position. As assembled, with reference again to FIGS. 2 and 3C, the retaining members 150 are disposed within the outer member 110 and aligned with respective slots 121, the bearing 140 is disposed in the distal portion 111b of the central bore 111, and the inner member 130 is positioned through the central bore 111 such that the tail 138 is disposed within the eccentric opening 141 of the bearing 140, the eccentric segments 136a extend through respective eccentric bores 151 of the retaining members 150, and the head 132 is disposed within the proximal portion 111a of the central bore 111. In the initial position, the retaining members 150 are fully disposed within the outer member 110.

With reference now to FIGS. 4A and 4B, the fixation device 100 is shown in a deployed position. To actuate the fixation device 100 from the initial position of FIG. 1 to the deployed position of FIGS. 4A and 4B, the inner member 130 is rotated, for example, in the direction of arrow "A", e.g., by inserting a driving instrument (not shown) having a male drive feature that is complementary in size and shape with the female drive feature disposed in the proximal end 132a of the head 132 of the inner member 130, thereby rotating the eccentric segments 136a (FIG. 2) of the cam shaft body 136 which, in turn, laterally displaces the retaining members 150 such that they extend outwardly through the slots 121 of the outer member 110.

In the deployed position, each engagement surface 152 of each retaining member 150 is disposed at about 90° from engagement surfaces 152 of adjacent retaining members 150. The engagement surfaces 152 cut or thread into osseous tissue as they are deployed during rotation of the inner member 130. The engagement surfaces 152 are secured to osseous tissue in the deployed position and inhibited from retreating back into the outer member 110 due to, for example, friction fit of the engagement surfaces 152 of the retaining members 150 with the osseous tissue and/or the angle of the engagement surfaces 152 in osseous tissue.

Figures 5, 6:
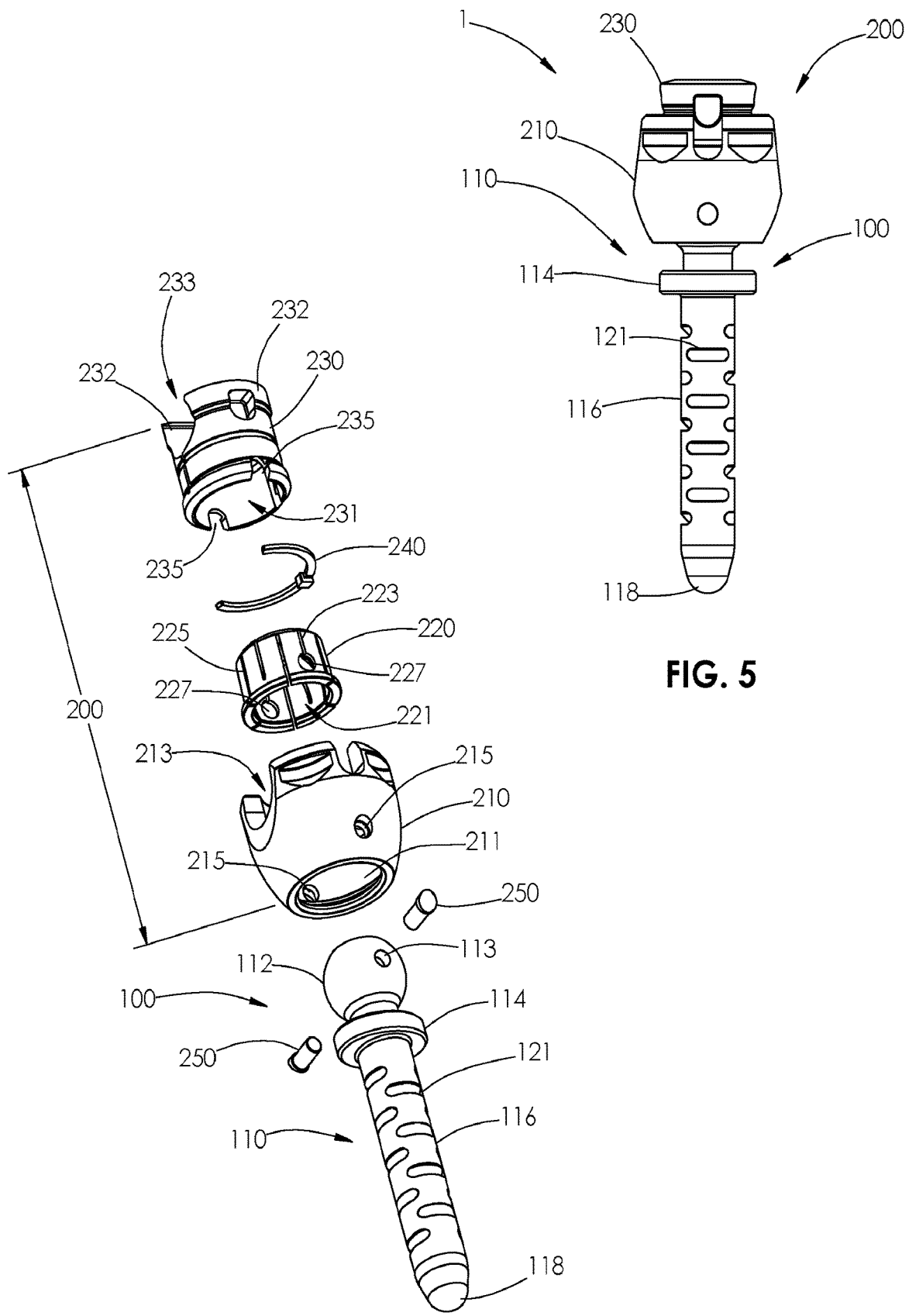
FIG. 5 is a side view of a fixation system including the fixation device of FIG. 1 and a modular attachment device in accordance with an embodiment of the present disclosure, shown in an initial position.
FIG. 6 is a perspective view of the fixation system of FIG. 5, with parts of the modular attachment device separated.

With reference now to FIG. 5, a fixation system 1 includes the fixation device 100 and a modular attachment device 200. The modular attachment device 200 is attached to the head portion 112 of the outer member 110 of the fixation device 100. The fixation device 100 is configured for use with a variety of modular attachment devices such as, for example, taper lock or set screw housing systems. Suitable taper lock or set screw housing systems include, for example, those shown in U.S. Pat. Nos. 8,814,919 and 9,393,049, the entire contents of each of which are incorporated by reference herein.

As shown in FIG. 6, the modular attachment device 200 has a taper lock arrangement and generally includes an outer housing 210, an intermediate housing 220, an inner housing or collet 230, and a retaining clip 240. The outer housing 210 has a generally annular body including an opening 211 defined axially therethrough. The intermediate housing 220 and the collet 230 each have a generally cylindrical body including respective openings 221, 231 defined axially therethrough.

The opening 221 of the intermediate housing 220 has a complementary configuration to the head portion 112 of the outer member 110 such that at least a portion of the head portion 112 is rotatably received within the opening 221. The intermediate housing 220 defines a plurality of slits 223, 225 configured to enable radial deflection at both ends of the intermediate housing 220. The intermediate housing 220 is disposed within the collet 230 and coupled thereto via the retaining clip 240 such that the intermediate housing 220 and the collet 230 are rotatable relative to each other while inhibiting relative axial movement therebetween.

The collect 230 includes a pair of upstanding wings 232 defining a saddle 233 having a generally u-shaped configuration. The saddle 233 is configured and dimensioned for receiving a spinal rod (not shown). The outer housing 210 is configured to slidably engage the collect 230 to releasably secure the spinal rod within the saddle 233 of the collet 230. The outer housing 210 also defines a saddle 213 having a generally u-shaped configuration to accommodate the spinal rod therein.

The intermediate housing 220 and the collet 230 are seated atop the head portion 112 of the fixation device 100, and the combination of the intermediate housing 220, the collet 230, and the head portion 112 are inserted into the outer housing 210. Pins 250 are positioned through bores 215 defined in the outer housing 210, bores 227 defined in the intermediate housing 220, slots 235 defined in the collet 230, and the recesses 113 of the head portion 112 of the fixation device 100 to facilitate and secure sliding movement of the fixation device 100 relative to the collet 230. The pins 250 are also configured to maintain rotational alignment between the modular attachment device 200 and the fixation device 100.

With reference now to FIGS. 7A-7C, the fixation system 1 is shown with the fixation device 100 in the deployed position. As specifically shown in FIG. 7B, the proximal end 132a of the head 132 of the inner member 130 of the fixation device 100 is accessible through the modular attachment device 200 such that the inner member 130 of the fixation device 100 may be rotated, as described above, to deploy the engagement surfaces 152 of the retaining members 150 of the fixation device 100 through the slots 121 of the outer member 110.

In a method of inserting a fixation device into osseous tissue, a clinician drills or otherwise forms a hole into osseous tissue using known devices and techniques (e.g., punching, cutting, coring, etc.). The fixation device 100, disposed in the initial position of FIG. 1, is inserted into the hole. The clinician may align the flange 114 of the fixation device 100 with the osseous tissue surrounding the hole, such as a pedicle, and insert the distal tip 118 and the elongated body portion 116 of the fixation device 100 into the hole until the flange 114 abuts the surface of osseous tissue. In the initial position, the engagement surface 152 of each retaining member 150 is disposed within the outer member 110 of the fixation device 100.

Once the fixation device 100 is inserted into osseous tissue, the inner member 130 of the fixation device 100 is manipulated by imparting a rotation force thereto. As discussed above, the inner member 130 is disposed within the central bore 111 of the outer member 110, with the eccentric segments 136a of the cam shaft body 136 disposed within the eccentric bores 151 of the retaining members 150. As the inner member 130 is rotated (e.g., via a driving instrument as discussed above), the retaining members 150 move from the initial position to the deployed position as shown in FIGS. 4A and 4B. In the deployed position, the retaining members 150 are laterally displaced by the rotation of the eccentric segments 136a of the cam shaft body 136 such that the engagement surfaces 152 of the retaining members 150 extend through the slots 121 of the outer member 110. In particular, the rotation of the inner member 130 causes the engagement surface 152 of each retaining member 150 to cut and/or thread into osseous tissue as the engagement surface 152 is deployed outwardly and away from the outer member 110.

In embodiments, the fixation device 100 is fully inserted into osseous tissue when the elongated body portion 116 is disposed within osseous tissue, the flange 114 abuts the outer surface of osseous tissue, and the retaining members 150 are deployed and engaged with osseous tissue, as described above. Advantageously, securement of the fixation device 100 is achieved with minimal rotational driving effort as compared to the multiple rotations required to distally advance and fully insert a tradition pedicle screw.

The outer member 110 of the fixation device 100 may also be manipulated after the initial manipulation of the inner member 130 by imparting a rotation force thereto. A rotational force may be applied to the outer member 110 (e.g., to the head portion 112) to cause the deployed engagement surfaces 152 of the retaining members 150 to cut and/or thread through additional tissue at the insertion site.

One of ordinary skill in the art will appreciate that any combination of manipulating the inner and outer members 130, 110 of the fixation device 100 can be used to cut and/or thread the fixation device 100 into osseous tissue at the insertion site. In particular, relative movement between the inner and outer members 130, 110 of the fixation device 100 may be utilized to deploy the retaining members 150. For example, the inner member 130 can be rotated about 90° clockwise from the initial position, and then the outer member 110 can be rotated about 90° counter-clockwise from its initial position resulting in the full deployment of the retaining members 150 to engage osseous tissue and secure the fixation device 100 within the opening in osseous tissue. Although 180° of relative movement between the inner and outer members 130, 110 is disclosed, it is envisioned that other ranges of relative movement between the inner and outer members 130, 110 (e.g., 90°) are contemplated for deploying the retaining members 150. This allows the clinician to insert the fixation device 100 within the opening in osseous tissue and use a combination of rotating the inner member 130 and the outer member 110 to provide precise alignment of an attachment device such as the modular attachment device 200 with a spinal rod.

In embodiments, a surgical device, such as the modular attachment device 200 of FIG. 5, may be coupled to the fixation device 100 such that other surgical devices (e.g., rods, plates, etc.) may be coupled thereto.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A fixation device comprising: an outer member including an elongated body portion defining a central bore through at least a portion thereof that extends along a central longitudinal axis, the elongated body portion including a slot defined therethrough; a retaining member disposed within the outer member when in an initial position and extending through the slot of the outer member when in a deployed position; and an inner member including a cam shaft body disposed within the central bore of the outer member, the cam shaft body coupled to the retaining member such that rotation of the inner member relative to the retaining member causes the retaining member to translate radially outward between the initial and deployed positions.

2. The fixation device according to claim 1, wherein the outer member includes a head portion disposed proximal to the elongated body portion, and a proximal portion of the central bore is disposed within the head portion.

3. The fixation device according to claim 2, wherein the outer member includes a flange disposed between the head portion and the elongated body portion, the flange having a transverse dimension that is greater than a transverse dimension of the elongated body portion.

4. The fixation device according to claim 1, wherein the outer member includes a distal tip disposed distal to the elongated body portion, and a distal portion of the central bore is disposed within the distal tip.

5. The fixation device according to claim 2, wherein the inner member includes a head disposed proximal to the cam shaft body, the head positioned within the proximal portion of the central bore.

6. The fixation device according to claim 5, wherein the head of the inner member is concentric with the proximal portion of the central bore.

7. The fixation device according to claim 5, wherein the inner member includes an elongated neck disposed between the head and the cam shaft body.

8. The fixation device according to claim 5, wherein the head of the inner member includes a proximal end including a recessed drive feature.

9. The fixation device according to claim 4, wherein the inner member includes a tail disposed distal to the cam shaft body, the tail positioned within the distal portion of the central bore.

10. The fixation device according to claim 9, wherein the tail is offset with respect to the central longitudinal axis and disposed within an eccentric opening of a bearing that is positioned in the distal portion of the central bore.

11. The fixation device according to claim 10, wherein the bearing is concentric with the distal portion of the central bore.

12. The fixation device according to claim 1, wherein the cam shaft body of the inner member includes an eccentric segment that is offset with respect to the central longitudinal axis.

13. The fixation device according to claim 12, wherein the retaining member defines an eccentric bore therethrough that receives the eccentric segment of the cam shaft body such that rotation of the inner member causes the eccentric segment to rotate about the central longitudinal axis which laterally moves the retaining member.

14. The fixation device according to claim 1, wherein the retaining member includes an engagement surface configured to cut or thread into osseous tissue as the retaining member is moved from the initial position to the deployed position.

15. The fixation device according to claim 14, the engagement surface includes a first side and a second side terminating at an edge.

16. The fixation device according to claim 15, wherein at least one of the first or second sides is angled.

17. The fixation device according to claim 15, wherein the edge is a blade.

18. The fixation device according to claim 12, wherein the eccentric segment has a cross-sectional area normal to the central longitudinal axis, a centroid of the cross-sectional area being offset with respect to the central longitudinal axis.

19. The fixation device according to claim 1, further including a plurality of retaining members, and wherein the elongated body of the outer member includes a plurality of slots.

20. The fixation device according to claim 19, wherein the plurality of slots is arranged in rows, and each row includes two slots of the plurality of slots disposed in opposed relation relative to each other.

21. The fixation device according to claim 20, wherein the two slots of each row are disposed at about 90° relative to the two slots in an adjacent row.

22. The fixation device according to claim 19, wherein the cam shaft body includes a plurality of eccentric segments each laterally offset with respect to the central longitudinal axis of the outer member.

23. The fixation device according to claim 22, wherein each eccentric segment of the plurality of eccentric segments extends through an eccentric bore defined through a retaining member of the plurality of retaining members such that rotation of the inner member causes the eccentric segments to rotate about the central longitudinal axis which laterally moves the retaining members between the initial and deployed positions.

24. A fixation system comprising: the fixation device according to claim 1; and a modular attachment device secured to the outer member of the fixation device.

25. The fixation system according to claim 24, wherein the outer member includes a head portion disposed proximal to the elongated body portion, the head portion supporting the modular attachment device thereon.

26. The fixation system according to claim 25, wherein the modular attachment device is pivotably mounted on the head portion of the outer member.

27. The fixation system according to claim 24, wherein the modular attachment device is a housing assembly.

28. A method of securing a fixation device to osseous tissue, comprising: inserting an elongated body portion of an outer member of a fixation device into a hole in osseous tissue, the elongated body portion defining a central bore through at least a portion thereof that extends along a central longitudinal axis, the elongated body portion including a slot defined therethrough; rotating an inner member of the fixation device that is disposed within the central bore of the outer member, the inner member including a cam shaft body coupled to a retaining member of the fixation device that is disposed within the outer member in an initial position, the rotation of the inner member moving the retaining member to a deployed position in which the retaining member extends through the slot of the outer member and cuts or threads into the osseous tissue surrounding the hole; and rotating the outer member of the fixation device after rotating the inner member such that the deployed retaining member further cuts or threads through the osseous tissue.

29. The method according to claim 28, further comprising abutting a distal surface of a flange of the outer member, which is disposed proximal to the elongated body portion, against the osseous tissue to limit the insertion depth of the elongated body portion into the hole.

30. The method according to claim 28, further comprising attaching a modular attachment device to a head portion of the outer member, the head portion disposed proximal to the elongated body portion.

* * * * *